United States Patent [19]

Isozaki

[11] Patent Number: 6,115,117
[45] Date of Patent: Sep. 5, 2000

[54] METHOD AND APPARATUS FOR SURFACE INSPECTION

[75] Inventor: Hisashi Isozaki, Tokyo, Japan

[73] Assignee: Kabushiki Kaisha Topcon, Tokyo, Japan

[21] Appl. No.: 09/190,442

[22] Filed: Nov. 13, 1998

[30] Foreign Application Priority Data

Nov. 21, 1997 [JP] Japan .................................. 9-336582

[51] Int. Cl.⁷ .................................................. G01N 21/00
[52] U.S. Cl. .................. 356/237.4; 356/376; 250/559.41
[58] Field of Search ............................ 356/237.1, 237.2, 356/237.3, 237.4, 237.5, 375, 376, 239.1, 239.2; 250/559.27, 559.31, 559.41

[56] References Cited

U.S. PATENT DOCUMENTS

| | | | |
|---|---|---|---|
| 4,831,274 | 5/1989 | Kohno et al. | 250/559.49 |
| 4,902,131 | 2/1990 | Yamazaki et al. | 356/237.2 |
| 5,576,831 | 11/1996 | Nikoonahad et al. | 356/375 |
| 5,715,052 | 2/1998 | Fujino et al. | 356/237.2 |

FOREIGN PATENT DOCUMENTS 8-145620  6/1996  Japan .

*Primary Examiner*—Hoa Q. Pham
*Attorney, Agent, or Firm*—Foley & Lardner

[57] ABSTRACT

A method and an apparatus, in which a light beam from a light source is provided on the surface of a semiconductor wafer through an optical system, a scattered light beam reflected from the surface of the semiconductor wafer is sensed, the semiconductor wafer and the optical system, in the meantime, are given a relative displacement with respect to each other, the foreign matter on the surface of the semiconductor wafer is inspected, and the position coordinates of the foreign matter are recorded. The height of the semiconductor wafer is measured when the foreign matter on the surface of the semiconductor wafer is inspected and the position coordinates of the foreign matter are corrected by utilizing the height signal of the semiconductor wafer.

11 Claims, 4 Drawing Sheets

METHOD AND APPARATUS FOR SURFACE INSPECTION

TECHNICAL BACKGROUND

The present invention relates to a method of inspecting the surface of an object of measurement, such as a semiconductor wafer, and an apparatus for carrying out the method.

In a prior art method for inspecting the surface of a semiconductor wafer, a light beam from a light source is thrown on the surface of the wafer through an optical system, a scattered light beam reflected from the surface of the wafer is sensed by a photoelectric converting element through another optical system, the wafer and the optical systems, in the meantime, are given relative displacement to each other, a foreign matter on the surface of the wafer is inspected, and, when a foreign matter is detected, the position coordinates of the foreign matter are recorded.

However, when a foreign matter on the wafer surface is inspected, if there is a warp in the wafer, the position coordinates of the foreign matter in the planar directions, of the detected three-dimensional position coordinates of the foreign matter, are detected and recorded, deviated from the reference plane due to the warp in the wafer.

SUMMARY OF THE INVENTION

An object of the invention is to provide a method and apparatus for surface inspection capable of detecting and recording accurately the position coordinates of a foreign matter in the planar directions even if there is a warp in the wafer.

In the present invention, the position coordinates are corrected by using a height signal of an object of measurement, such as a wafer.

The invention is such that it corrects the detected position of a foreign matter by means of software on the basis of height information of the wafer.

When there is a warp in the wafer, the deviation in the direction of the height of the wafer surface from the reference plane becomes greater accordingly as the point under consideration comes near the center of the warp. Therefore, the position coordinates of the foreign matter in the planar directions are wrongly detected and recorded.

Accordingly, in the present invention, the change of the wafer surface in the direction of the height is measured and thereby the positional information of the foreign matter is corrected. Namely, when a foreign matter is inspected on the wafer surface, the height of the wafer is measured and the position coordinates of the foreign matter are corrected by utilizing the height signal of the wafer. For example, the height of the wafer is measured at all times while the wafer surface is inspected for a foreign matter thereon and, when a foreign matter is detected, the detected position coordinates of the foreign matter are corrected by utilizing the height of the wafer at that time.

The height'signal (information) of the wafer can be obtained by an auto focus means for automatically focusing light beams provided on the wafer surface. In the present invention, it is preferred that the height signal (information) of the wafer obtained by the auto focus means be utilized. Although such an auto focus means has so far been used for stabilizing the sensitivity, it is utilized here as a means for correcting the height signal (information). Thereby, it is made possible to have the sensitivity to a foreign matter kept in conformity with a warp in the wafer and maintained at the optimal level. Besides, such an additional effect can be obtained that the position coordinates of the foreign matter can be corrected by utilizing the height signal of the wafer.

According to an aspect of the invention, a light beam from a light source is provided on the surface of a wafer through an optical system, a scattered light beam reflected from the surface of the wafer is sensed, the wafer and the optical system, in the meantime, are given a relative displacement with respect to each other, the foreign matter on the surface of the wafer is inspected, and the position coordinates of the foreign matter are recorded. The height of the wafer is measured when the foreign matter on the surface of the wafer is inspected and the position coordinates of the foreign matter are corrected by utilizing the height signal of the wafer.

According to another aspect of the invention, a light beam from a light source is provided on the surface of an object of measurement, for example a wafer, through an optical system, a scattered light beam reflected from the surface of the wafer is sensed, the wafer and the optical system, in the meantime, are given a relative displacement with respect to each other, the foreign matter on the surface of the wafer is inspected, and the position coordinates of the foreign matter are recorded. Specifically, the height of the wafer is constantly measured while the surface of the wafer is being inspected for a foreign matter thereon, and, when a foreign matter is detected, the position coordinates of the foreign matter in the planar directions, at least, of the detected position coordinates of the foreign matter are corrected by utilizing the obtained height of the wafer.

According to a further aspect of the invention, an apparatus for surface inspection carrying out the above described method of surface inspection comprises a light source, an irradiating optical system for providing a light beam from a light source on the surface of an object of inspection, a light receiving optical system for receiving a reflected light beam from the object of inspection, a photosensing portion for sensing the reflected light beam received by the light receiving optical system, and a signal processing portion setting up a threshold signal for processing the signal from the photosensing portion.

DESCRIPTION OF THE PREFERRED EMBODIMENTS

Figure 1:
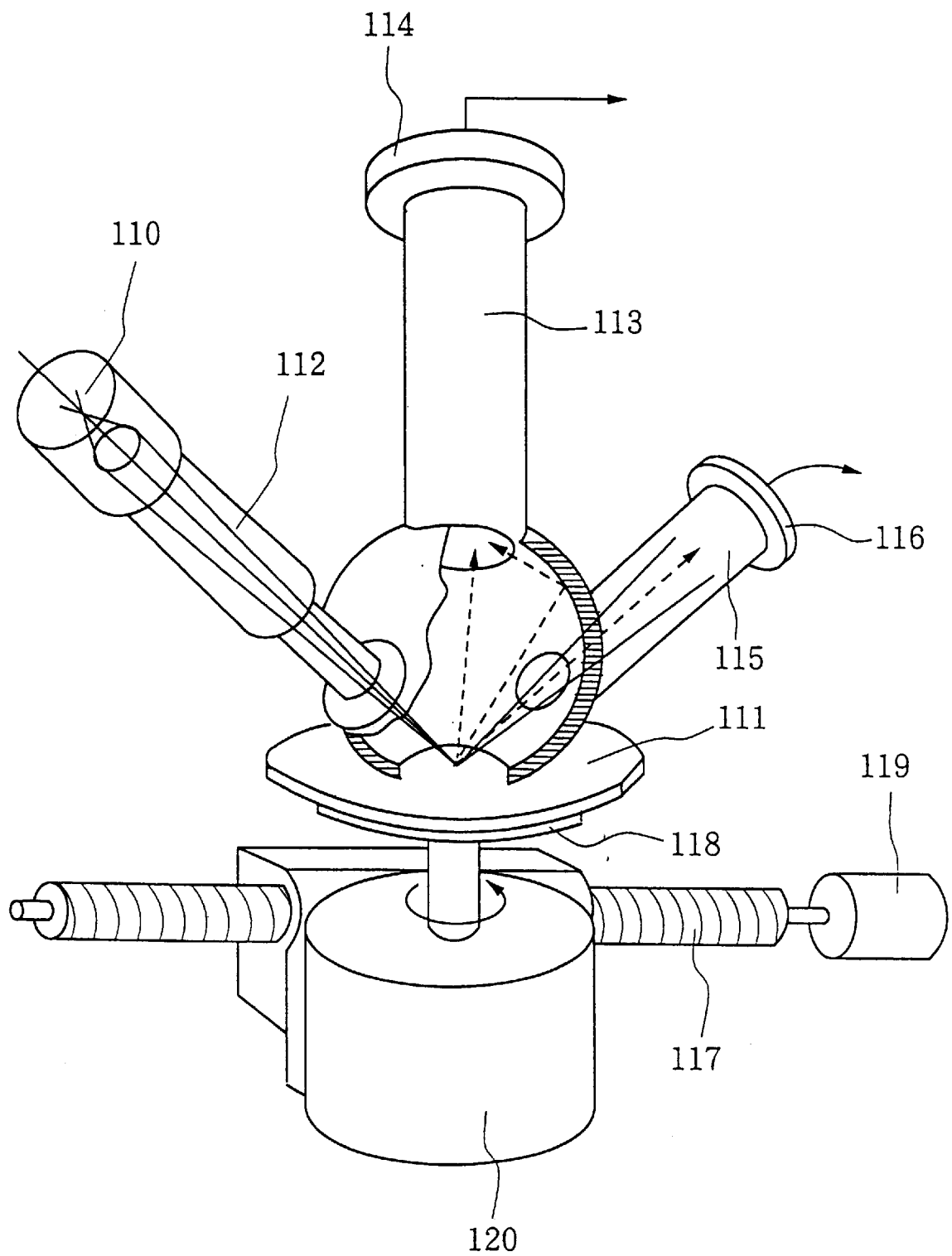
FIG. 1 is a drawing showing an example of a surface inspection apparatus of the invention.

FIG. 1 shows an example of a surface inspection apparatus on a spiral scanning system according to the invention. It comprises a light source 110, an irradiating optical system 112 for providing a light beam from the light source 110 onto the surface of a wafer 111 as an object of measurement, a first light receiving optical system 113 receiving a scattered light beam reflected from a foreign matter on the surface of the wafer 111 irradiated by the irradiating optical system 112 for forming a received-light signal, a photoelectric converting element 114 for outputting the received light by the light receiving optical system 113 as a first sensed-light signal, a second light receiving optical system 115 for receiving and condensing a light beam reflected by mirror reflection from the surface of the wafer 111 irradiated by the irradiating optical system 112, a photosensing portion 116 for outputting the position of the reflected light beam condensed by the second light receiving optical system 115, a linear displacement portion 117 for providing the surface of the wafer 111 and the irradiating optical system 112, plus the first and second light receiving optical systems 113 and 115, with linear relative displacement to each other, and a rotational displacement portion 118 for providing the surface of the wafer 111 and the irradiating optical system 112, plus the first and second light receiving optical systems 113 and 115, with a rotational relative displacement with respect to each other, such that the irradiating light beam makes a spiral scan of the surface of the wafer 111. The linear displacement portion 117 and the rotational displacement portion 118 are coupled with motors 119 and 120, respectively.

The output of the photosensing portion 116 is such that it indicates the position of the reflected light beam following a change in the height of the object of measurement. It is formed of a position sensitive detector (PSD), a linear sensor, an area sensor, or the like.

The method of detecting the position in the direction of the height is well known as the optical lever method.

Figure 2:
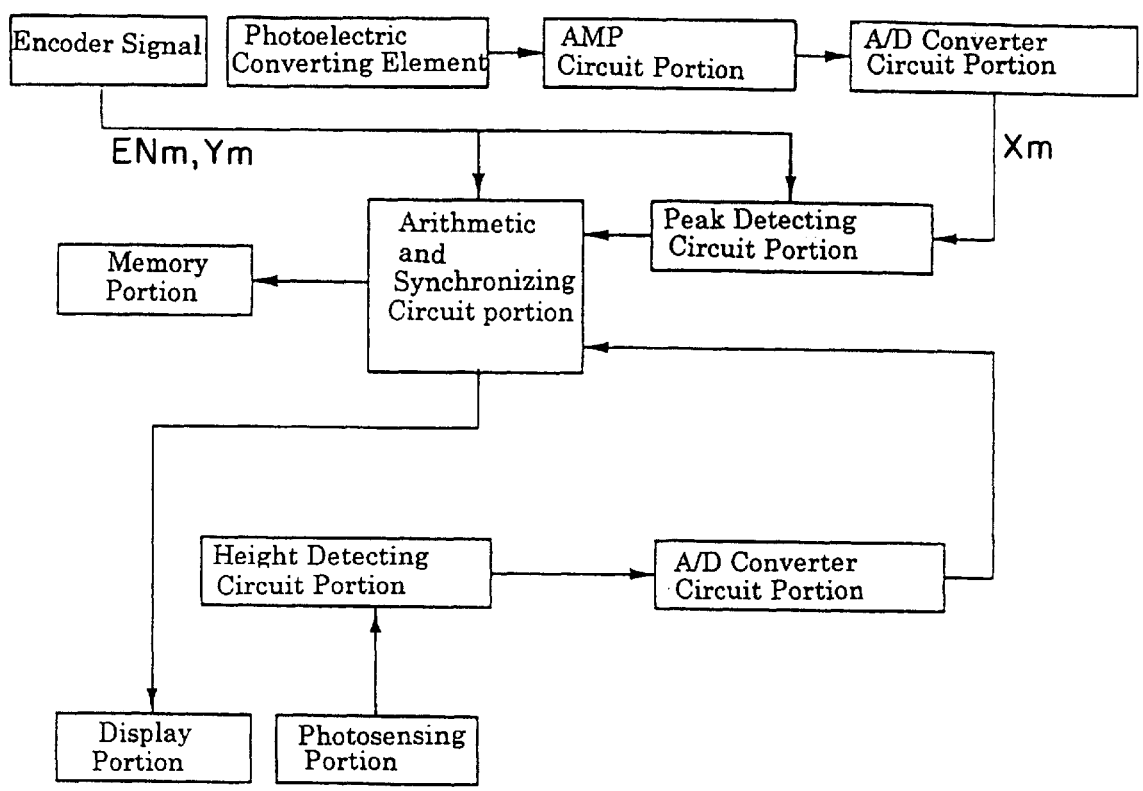
FIG. 2 is a block diagram showing an embodiment of the invention.

Referring to FIG. 2, the output signal from the photoelectric converting element is transmitted, through the AMP circuit portion and A/D converter circuit portion, to the peak detecting circuit portion, wherein the signal is subjected to a peak detecting process and thereafter sent to the arithmetic and synchronizing circuit portion.

The signal from the photosensing portion 116 is input, through the height detecting circuit portion and A/D converter circuit portion, to the arithmetic and synchronizing circuit. This signal corresponds to the height information of the wafer.

The arithmetic and synchronizing circuit portion makes a predetermined correction for the coordinates of the foreign matter on the basis of the height signal of the wafer. The measurement data of the foreign matter after the correction is stored in the memory portion and displayed on the display portion according to the need.

Figure 4:
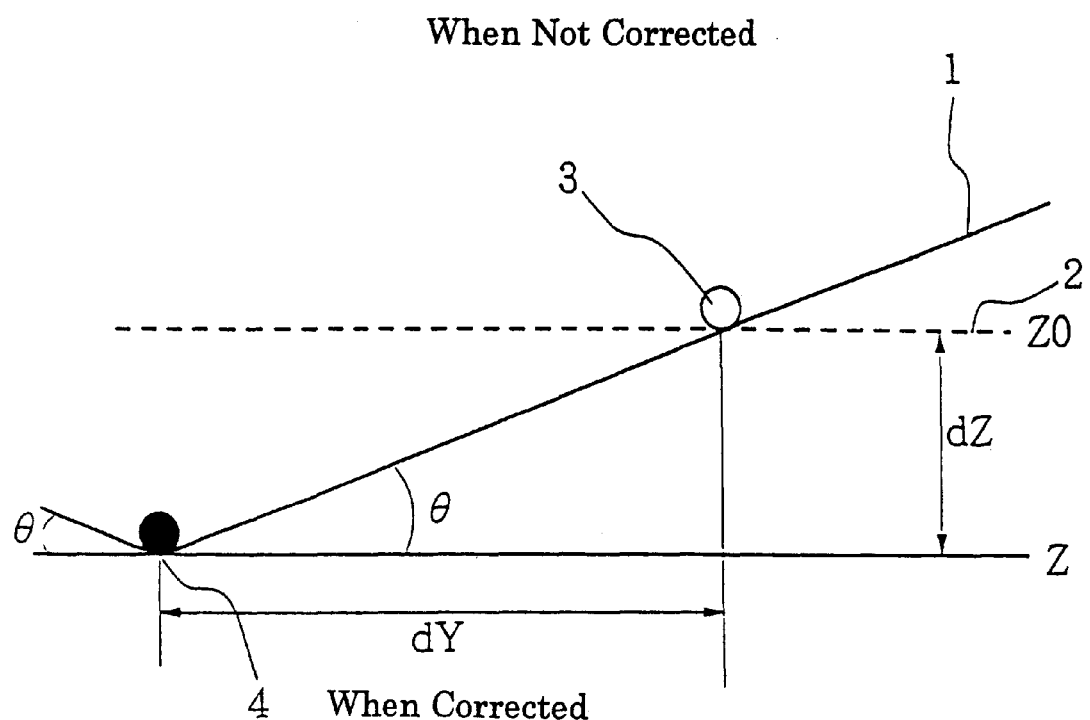
FIG. 4 is a method of correction made when a wafer has a change in height.

FIG. 4 shows an example of the method for correcting position coordinates employed in the method of wafer surface inspection according to the invention.

In the method of wafer surface inspection according to the invention, a light beam from a light source is providing on the surface of the wafer through an optical system, a scattered light beam reflected from the surface of the wafer is sensed by a photoelectric converting element through an optical system, the wafer and the optical systems, in the meantime, are given a relative displacement with respect to each other, a foreign matter on the wafer surface is inspected, and the three-dimensional position coordinates of the foreign matter are recorded.

While the wafer surface is inspected for a foreign matter thereon, the height of the wafer is measured constantly. When a foreign matter has been detected, the height dependent position at this time is determined and this value is added to or subtracted from the position coordinate of the foreign matter in the planar direction, of the detected position coordinates of the foreign matter, to thereby perform the correction. According to the need, the position of the wafer in another direction is also corrected in conformity with the correction in the position of the wafer by the height dependent position.

For example, when there is an upward warp in the wafer, the surface of the wafer has a greater deviation in the direction of the height above the reference plane accordingly as the point under consideration comes near the central portion. Therefore, the position coordinate of the foreign matter in the direction of the height is detected and recorded with the deviation corresponding to the upward warp included.

FIG. 4 shows an example of the correction of position coordinates on the basis of position information of the foreign matter in the planar direction. A light beam 1 from a light source is providing on the surface of a wafer through an optical system and a scattered light beam reflected from the wafer surface is sensed by a photoelectric converting element through an optical system (not shown).

Therefore, in the present invention, a change of the wafer surface in the direction of the height is measured by a known auto focus means and, thereby, the position coordinates of the foreign matter in the planar direction and, according to the need, the position coordinate thereof in another direction are corrected.

Figure 3:
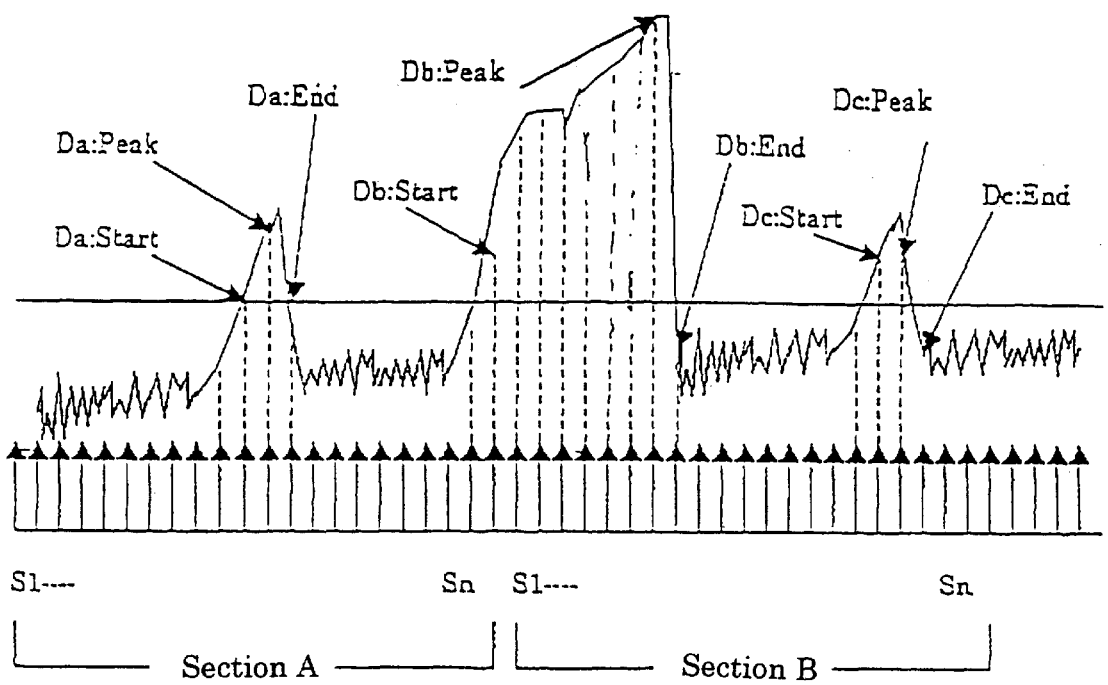
FIG. 3 is a diagram showing an output of a photoelectric converting element containing scattered light signals from foreign matters.

Shown in FIG. 3 is an example of the sensed-light signal including scattered light beams from foreign matters obtained by the photoelectric converting element while spiral scanning is carried out by the apparatus for surface inspection of FIG. 1.

When the peak detecting circuit portion of FIG. 2 detects, in accordance with the signal from the photoelectric converting element, that the scattered-light signal from a foreign matter has exceeded a slice level while the scanning is being made, judges the point of time as the starting position. Thereupon, it outputs coordinate data, i.e., ENm start data according to the signal from an encoder, Ym start data according to the displacement of the linear displacement portion 117, and Xm start data according to the clock signal from a clock circuit CLK.

When, thereafter, the scattered-light signal from the foreign matter falls below the slice level, it determines this point as the ending position. Thereupon, it outputs the position data, i.e., ENm end data according to the signal from the encoder, Ym end data according to the displacement of the linear displacement portion 117, and Xm end data according to the clock signal from the clock circuit CLK.

The point between the starting position and the ending position at which the scattered-light signal from the foreign matter is at its maximum is judged as the peak, and the value of the peak level and the coordinates, i.e., ENm data according to the signal from the encoder, Ym data according to the displacement of the linear displacement portion 117, Xm data according to the clock signal from the clock circuit CLK, and Dm peak as the peak level, are output.

While a foreign matter on the surface of the wafer is inspected, when it is found that the height of the wafer has a deviation of dZ referenced from the reference plane 2 as shown in FIG. 4 in accordance with the output signal from the photosensing portion 116, the arithmetic and synchronizing circuit portion makes a correction for the coordinates Ym . . . in the radial direction obtained by the peak detecting circuit portion by an amount of $$dY = dZ/\tan\theta,$$

where $\theta$ denotes the angle formed between the light beam incident on the reference plane and the reference plane.

For example, the coordinate of the peak after the correction is given by Ym data−dY.

Although a discrepancy in the coordinate value occurs only in the radial direction in the case of the spiral scanning, similar correction can be made in the case of other scanning systems to the coordinate values in the directions in which discrepancies are produced due to a change in height.

In these days, the scanning electron microscope (SEM) is used in many cases because of its stable sensitivity and increase in practicing of observation of the foreign matter and analysis of its components by instrument of analysis. However, since the SEM has a narrow visual field while it has a high resolving power, it requires much time to detect a foreign matter. Therefore, more accurate position information (coordinates) in its data is required of a foreign matter detection apparatus.

The measurement apparatus, even when it is applied to the measurement of an object whose surface conditions are diversified, must have an improved detecting sensitivity, and therefore, it is designed to be affected by the surface conditions as little as possible. As a result, it has become necessary to cast the light beam from a low angle of incidence.

Further, with the increase in diameter of the object of measurement and in consideration of the backside of the same, it is difficult to support the object of measurement on a plane and, hence, the object under measurement tends to loose its levelness.

In the embodiments, when the foreign matter is detected, the horizontal position coordinates of the foreign matter may be corrected while the height of an object of measurement such as a semiconductor wafer is always measured. Further, only when the foreign matter is detected, the height of an object of measurement such as a wafer may be measured, and then the horizontal position coordinates of the foreign matter can be corrected by using the height signal of the foreign matter.

In view of such technical background, the advantageous effects achieved by the invention as described below are considered significant:

(1) More accurate coordinate data of detected foreign matters than in prior art apparatuses can be obtained, not affected by the use of an optical system of a low angle of incidence and by existence of a distortion or warp in the object of measurement (wafer) due to the increase in diameter or the supporting method thereof.

(2) The time for observation and analysis of the object by the use of an SEM or the like can be shortened because of improvement in the accuracy of the coordinate data that are obtained.

What is claimed is:

1. A method for inspecting a surface of an object to be measured, comprising the steps of:

projecting a light beam from a light source on the surface of the object by means of an optical system;

sensing a scattered light beam reflected from the surface of the object;

sensing a mirror-reflected light beam mirror-reflected from the surface of the object when the object is irradiated by said irradiating optical system;

moving the object relative to the optical system;

inspecting a foreign matter on the surface of the object;

detecting a height of the object from the mirror-reflected light beam; and recording position coordinates of the foreign matter, wherein the height of the object is measured so as to produce a height signal of the object when the foreign matter on the surface of the object is inspected, and then the position coordinates of the foreign matter are corrected on the basis of the height signal of the object without adjusting the object.

2. A method for inspecting a surface of an object to be measured comprising the steps of:

projecting a light beam from a light source on the surface of the object by means of an optical system;

sensing a scattered light beam reflected from the surface of the object;

sensing a mirror-reflected light beam from the surface of the wafer irradiated by said optical system;

moving the object relative to the optical system;

inspecting a foreign matter on the surface of the object;

detection a height of the object from the mirror-reflection light beam; and recording position coordinates of the foreign matter, wherein the height of the object is constantly measured while the surface of the object is inspected and, when the foreign matter is detected, the position coordinates of the foreign matter are corrected at least in a planar direction on the basis of the height of the object without adjusting the object.

3. An apparatus for inspecting a surface of an object comprising:

a light source;

an irradiating optical system for projecting a light beam from the light source on the surface of the object;

a first light receiving optical system for receiving a scattered light reflected from the object;

a second light receiving optical system for receiving a mirror-reflected light beam from the surface of the object when the object is irradiated by said irradiating optical system;

a first sensing portion for sensing the scattered light received by said first light receiving optical system;

a second sensing portion for sensing the mirror-reflected light beam received by said second light receiving optical system; and a signal processing portion for recording position coordinates of the foreign matter, wherein a height of the object is measured on the basis of the mirror-reflected light beam when a foreign matter is detected on the surface of the object and wherein, the position coordinates of the foreign matter are corrected on the basis of the height of the object without adjusting the object.

4. An apparatus according to claim 3, wherein said second sensing portion delivers an output indicating the position of the mirror-reflected light beam, dependent on a change in height of the object.

5. An apparatus for inspecting a surface of an object comprising:

a light source;

an irradiating optical system for projecting a light beam from the light source on the surface of an object;

a first light receiving optical system for receiving a scattered light reflected from the object;

a second light receiving optical system for receiving a mirror-reflected light beam from the surface of the object irradiated by said irradiating optical system;

a first sensing portion for sensing the scattered light received by said first light receiving optical system;

a second sensing portion for sensing the mirror-reflected light beam received by said second light receiving optical system; and a signal processing portion for recording position coordinates of the foreign matter, wherein a height of the object of measurement is constantly measured while the surface of the object is inspected and, when a foreign matter is detected, the position coordinates of the foreign matter are corrected at least in a planar direction on the basis of the height of the object without adjusting the object.

6. An apparatus for inspecting a surface of a wafer comprising:

a light source;

an irradiating optical system for projecting a light beam from the light source on the surface of the wafer;

a first light receiving optical system for receiving a scattered light reflected from a foreign matter placed on the surface of the wafer when it is irradiated by said irradiating optical system thereby generating a received-light signal;

a photoelectric converting element for outputting the scattered light received by said first light receiving optical system as a first sensed-light signal;

a second light receiving optical system for receiving and condensing a mirror-reflected light beam from the surface of the wafer when it is irradiated by said irradiating optical system;

a photosensing portion for outputting the position of the mirror-reflected light beam condensed by said second light receiving optical system;

a signal processing portion for recording position coordinates of the foreign matter, wherein a height of the object of measurement is constantly measured while the surface of the object is inspected and, when a foreign matter is detected, the position coordinates of the foreign matter are corrected at least in a planar direction on the basis of the height of the object without adjusting the object;

a linear displacement portion for linearly displacing the surface of the wafer to said irradiating optical system, and said first and second light receiving optical systems; and a rotational displacement portion for rotationally displacing the surface of the wafer to said irradiating optical system, and said first and second light receiving optical systems.

7. An apparatus according to claim 6, wherein the light beam spirally scans the surface of the wafer.

8. An apparatus according to claim 6, wherein said linear displacement portion and said rotational displacement portion are each coupled with a motor.

9. An apparatus according to claim 6, wherein said photosensing portion delivers an output indicating the position of the mirror-reflected light beam, dependent on a change in height of the wafer.

10. An apparatus according to claim 6, wherein said photosensing portion is a position sensitive detector (PSD), a linear sensor, or an area sensor.

11. An apparatus according to claim 6, wherein an optical lever mechanism is employed for position detection in the direction of height.

* * * * *